United States Patent
Skelton et al.

(10) Patent No.: US 6,292,692 B1
(45) Date of Patent: Sep. 18, 2001

(54) MEDICAL TREATMENT DEVICE WITH FUNCTIONS, OPERATED UNDER PASSCODE CONTROL

(75) Inventors: Brian J. Skelton, Lake Zurich; Dean L. Milani, Highland Park; Michael C. Garrett, Skokie; William J. Smirles, Deerfield; Raymond Bender, Elgin; Robert A. Scheidt, Skokie, all of IL (US)

(73) Assignee: Medical Research Laboratories, Inc., Buffalo Grove, IL (US)

( * ) Notice: Subject to any disclaimer, the term of this patent is extended or adjusted under 35 U.S.C. 154(b) by 0 days.

(21) Appl. No.: 09/302,614

(22) Filed: Apr. 30, 1999

(51) Int. Cl.$^7$ .................................................. A61N 1/39
(52) U.S. Cl. ...................................... 607/5; 607/9; 607/2
(58) Field of Search ..................... 607/5, 9, 1–3

(56) References Cited

U.S. PATENT DOCUMENTS

| | | |
|---|---|---|
| 4,453,074 | 6/1984 | Weinstein . |
| 4,815,031 | 3/1989 | Furukawa . |
| 5,042,067 | 8/1991 | Moriyama . |
| 5,115,508 | 5/1992 | Hatta . |
| 5,226,137 | 7/1993 | Bolan et al. . |
| 5,442,553 | 8/1995 | Parrillo . |
| 5,495,411 | 2/1996 | Ananda . |
| 5,509,070 | 4/1996 | Schull . |
| 5,535,409 | 7/1996 | Larvoire et al. . |
| 5,594,227 | 1/1997 | Deo . |
| 5,606,315 | 2/1997 | Gaskins . |
| 5,611,048 | 3/1997 | Jacobs et al. . |
| 5,644,711 | 7/1997 | Murphy . |
| 5,652,793 | 7/1997 | Priem et al. . |
| 5,682,475 | 10/1997 | Johnson et al. . |
| 5,715,390 | 2/1998 | Hoffman et al. . |
| 5,737,421 | 4/1998 | Audebert . |
| 5,742,683 | 4/1998 | Lee et al. . |
| 5,751,950 | 5/1998 | Crisan . |
| 5,787,169 | 7/1998 | Eldridge et al. . |
| 5,802,176 | 9/1998 | Auebert . |
| 5,848,064 | 12/1998 | Cowan . |
| 6,021,349 | * 2/2000 | Arand et al. .............................. 607/5 |

\* cited by examiner

*Primary Examiner*—George R. Evanisko
(74) *Attorney, Agent, or Firm*—Fitch, Even, Tabin & Flannery

(57) ABSTRACT

A medical treatment device includes a plurality of digitally controlled medical treatment modules with a feature authorizing system to enable selected treatment modules in response to the entry and subsequent validation of a user's passcode.

20 Claims, 15 Drawing Sheets

System Block Diagram

Diagram of Password Protected Modes

==> PRESS FLASHING HOLD BUTTON FOR AN ADDITIONAL 60 SEC. WAIT PERIOD

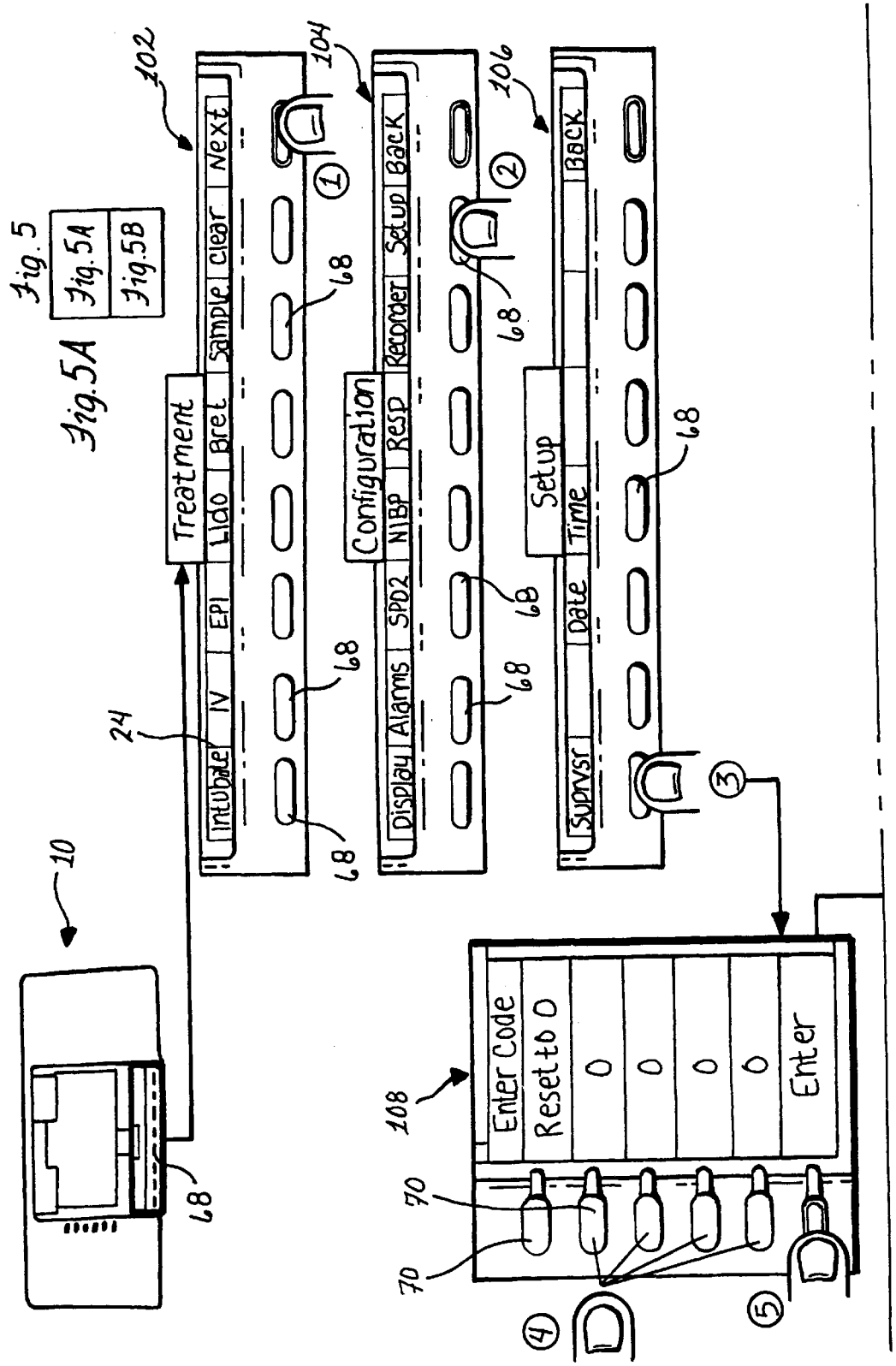

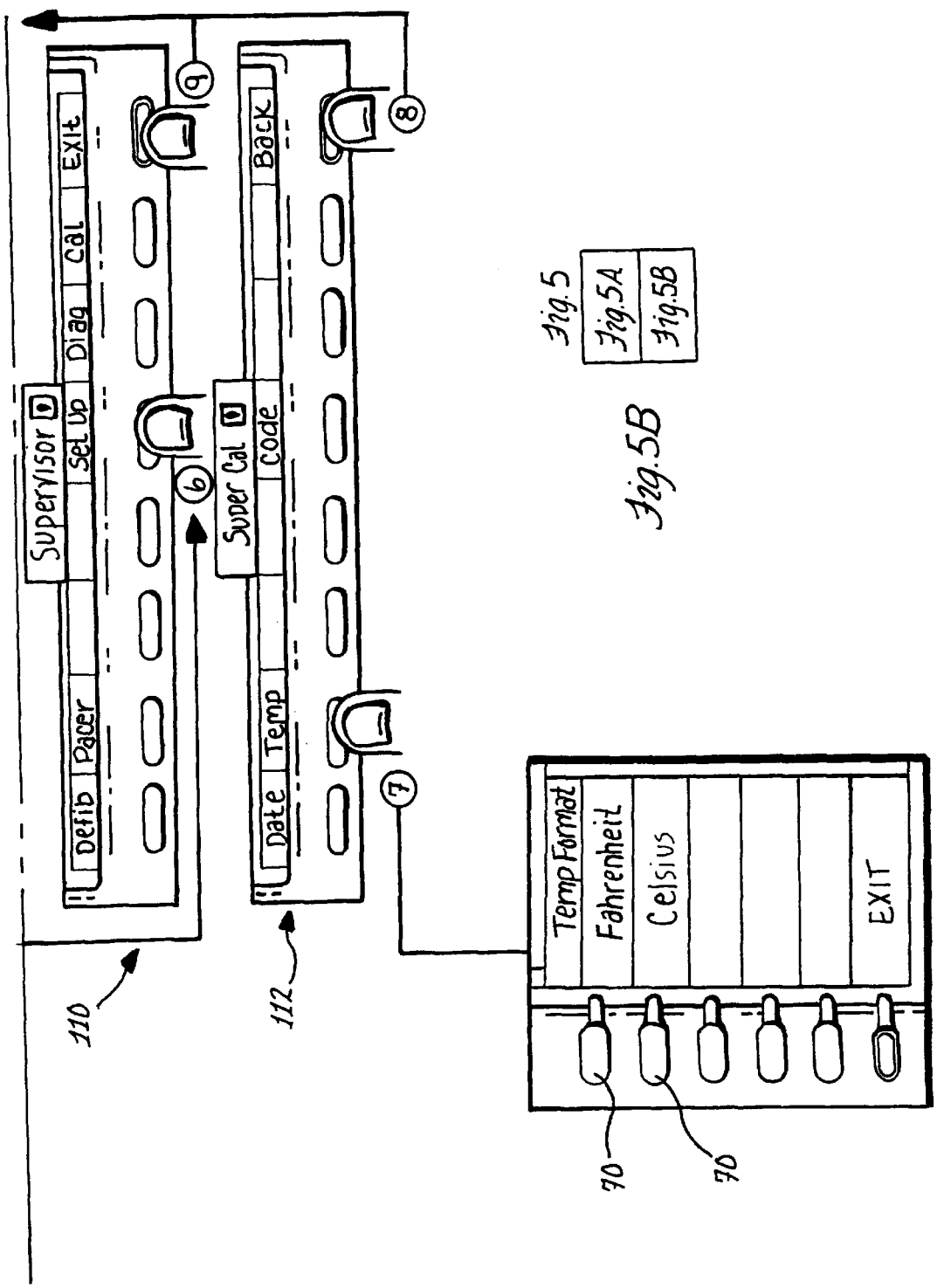

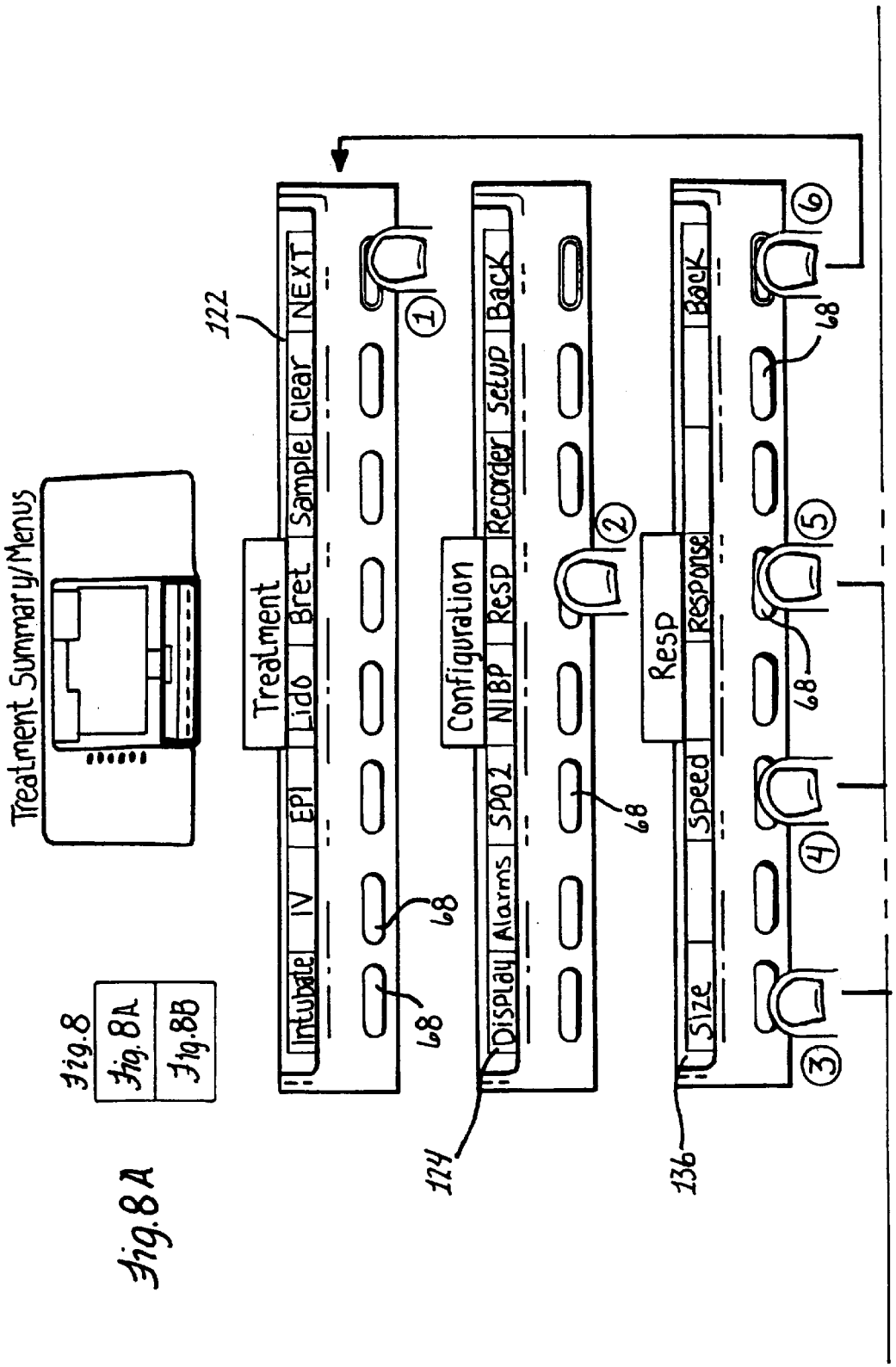

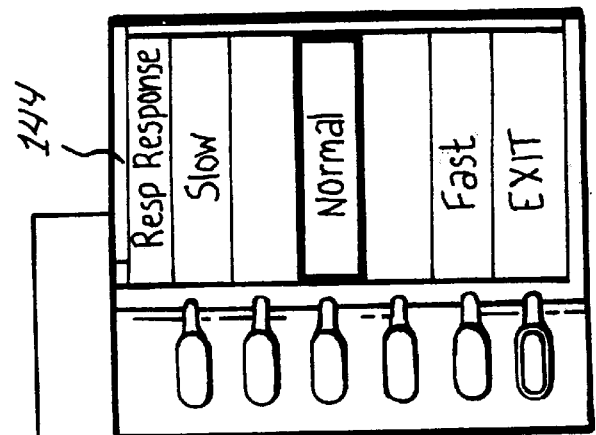
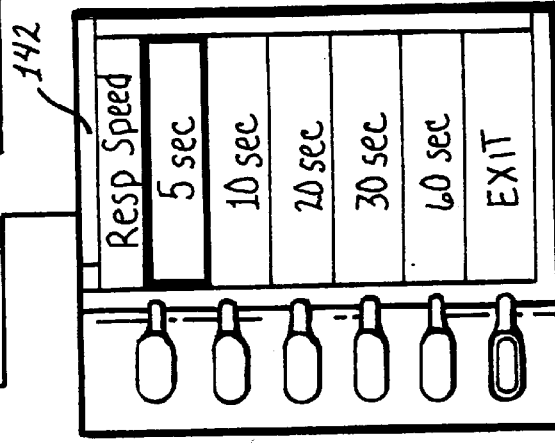
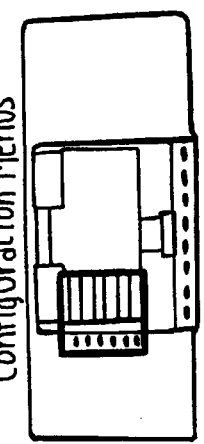
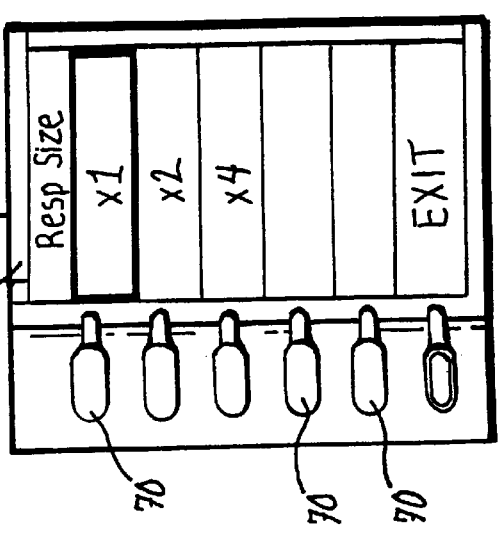
Fig. 8B

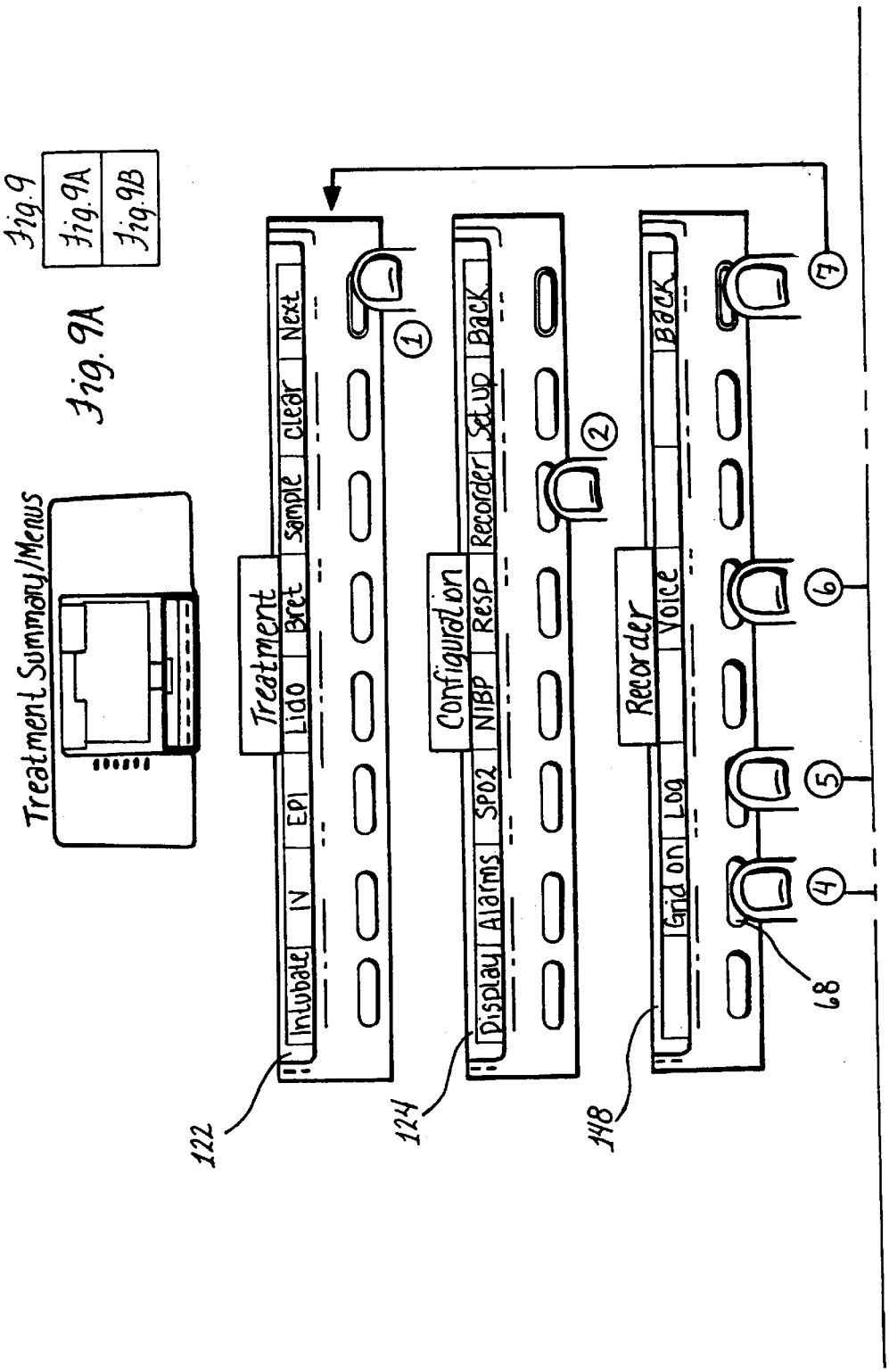

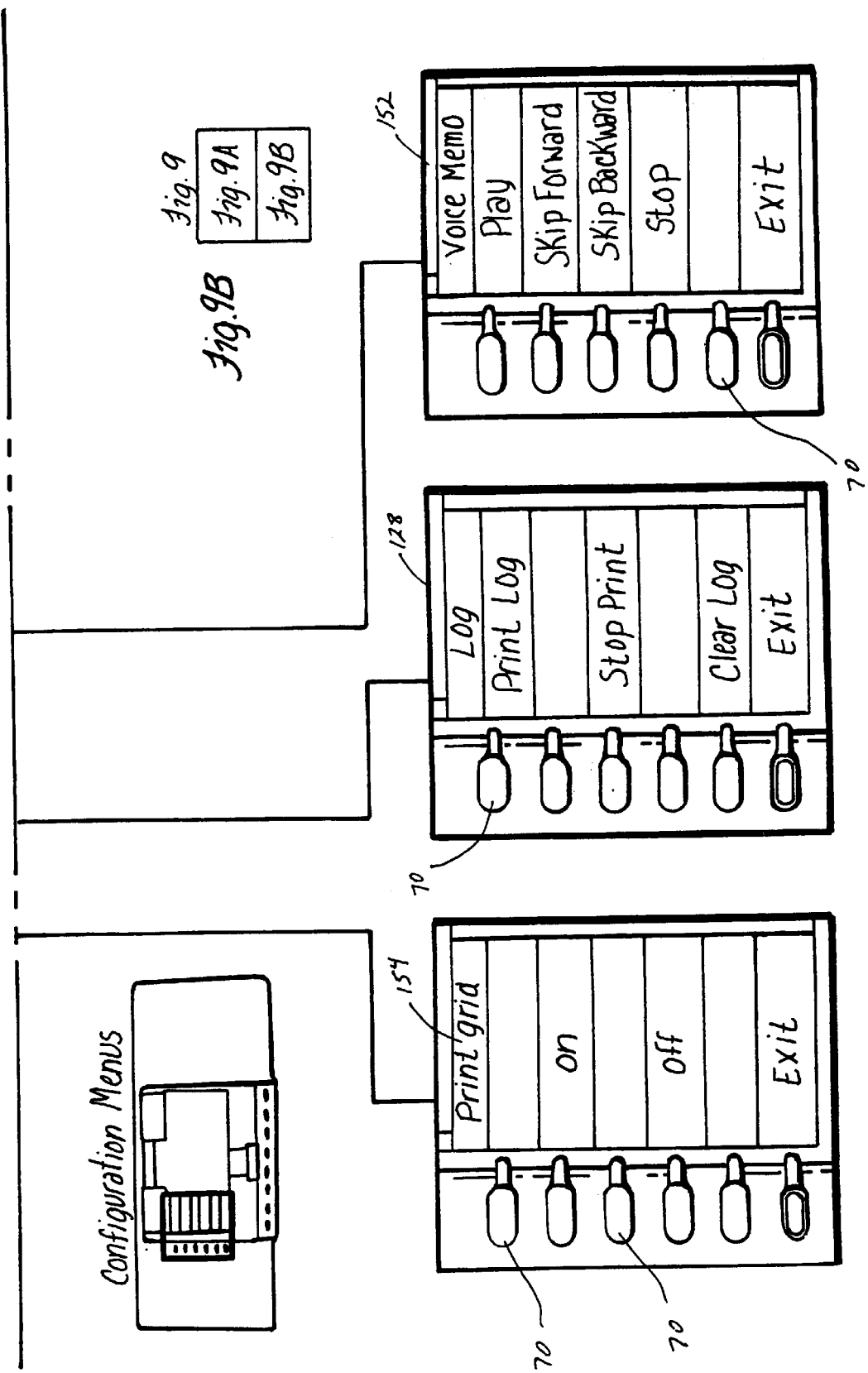

MEDICAL TREATMENT DEVICE WITH FUNCTIONS, OPERATED UNDER PASSCODE CONTROL

BACKGROUND OF THE INVENTION

1. Field of the Invention

The present invention relates to medical treatment devices, and in particular such devices which can be readily reconfigured for use by medical attendants having different levels of training.

2. Description Of The Related Art

With recent changes to the medical industry, patients are treated by teams of individuals having specialized assignments and corresponding specialized levels of training. In order to conserve resources and to minimize the cost of patient care, medical care givers are using automated or semi-automated equipment to an increasing extent to help them more efficiently address a patient's needs.

Whereas medical treatment in the past was administered in a controlled setting, such as that of a hospital or medical emergency clinic, medical care is increasingly administered in a wide variety of uncontrolled field conditions. Emergency medical technicians (EMTs) are now routinely employed in police and fire departments and various military units as well as ambulance and other first responder private service providers. In an era of increasing specialization and cost controls, it has been found desirable to employ EMTs having a level of training corresponding to the anticipated need for structured patient services.

One particularly important service provided by EMTs and other first responders is to deliver immediate medical attention in critical life threatening conditions, often occurring remote from hospitals or other controlled environments. Ears and other emergency care givers may be called upon to provide a number of different patient treatments, including monitoring cardiac activity and other vital patient conditions, administering drugs and other treatments as well as performing a variety of invasive and non-invasive diagnostic procedures.

Recent improvements have been made to medical treatment devices suitable for providing defibrillator therapy on an emergency basis. Most notably, manufacturers of such medical treatment devices have been able to incorporate expert analytical capability with transthoracic cardiac defibrillation so that care givers having little or no training can successfully administer cardiac defibrillator treatment in emergency situations where defibrillator intervention must be carried out within minutes to preserve a patient's life. Various legislative bodies have recognized the value of such medical intervention and the ability of automatic and semi-automatic external defibrillator devices to control shock therapy to the point where members of the general public can successfully intervene to preserve life in the midst of a cardiac emergency.

Patient monitoring equipment has also become automated to an increasing extent. Recent improvements in such equipment have found ready acceptance in hospital environments to aid in the reduction of the cost of patient care. Such equipment may be relied upon to provide relatively benign, non-intrusive observance of a patient's medical condition. The flexibility and safety record of such automated equipment has encouraged the use of automated equipment to also carry out more sensitive intrusive medical treatments. Due to the cost of construction, maintenance and routine expert calibration and other maintenance, such automated medical care devices have generally been limited to special purpose applications in an attempt to reduce costs.

Frequently, automated patient monitoring equipment is set up to automatically record various types of patient data observed on sensors coupled to the device. For certain medical treatment operations, such data may be recorded but not actually used at the time of the medical treatment, especially when care givers having lower levels of training are able to carry out their mission with assistance from expert functions of the device. Various types of data unrelated to the automated procedure may nonetheless be recorded and later downloaded for storage with the patient's records. It would be best if such data were not generated or, alternatively, certain warnings and precautions were implemented to avoid erroneous conclusions.

There is continuing interest in evaluating automated or semi-automated medical treatment devices, with a view toward expanding their role in reducing medical costs.

SUMMARY OF THE INVENTION

It is an object of the present invention to provide medical treatment devices of the automated and semi-automated type.

A further object of the present invention is to provide medical treatment devices which can carry out a number of different, sometimes unrelated tasks.

Another object of the present invention is to provide such devices having security and control capability to ensure that more advanced medical treatment is given only by appropriately trained personnel.

A further object of the present invention is to provide medical treatment devices which, while flexible in operation, provide an adequate level of patient confidentiality as well as preventing an inappropriate or misleading use of observed patient data.

These and other objects of the present invention which will become apparent from studying the appended description and drawings are provided in a medical treatment device, including:

a plurality of digitally controlled medical treatment modules arranged in multiple tiers, with at least one medical treatment module in each tier [and with at least one tier having a plurality of medical treatment modules];

a digital controller for controlling a plurality of medical treatment module;

memory storage means for storing memory data, associated with said digital control means;

data entry means for entering a user passcode;

comparator means for comparing the passcode data entered to the passcode data stored in said memory means;

means responsive to said comparator means determining the medical treatment modules available to the user and for delivering instructions to said digital controller to enable said authorized medical treatment modules; and at least some of said tiers of said medical treatment modules including entry means permitting entry from lower level tiers only upon user entry of an authorized passcode.

BRIEF DESCRIPTION OF THE DRAWINGS

FIG. 5 is a schematic diagram indicating a supervisor data entry procedure;

FIG. 8 is a schematic diagram indicating a key press sequence for configuring patient summary and menus;

FIG. 9 is a schematic diagram indicating a key press sequence for configuring recorder and print-out functions;

DETAILED DESCRIPTION OF THE PREFERRED EMBODIMENTS

Figure 1:
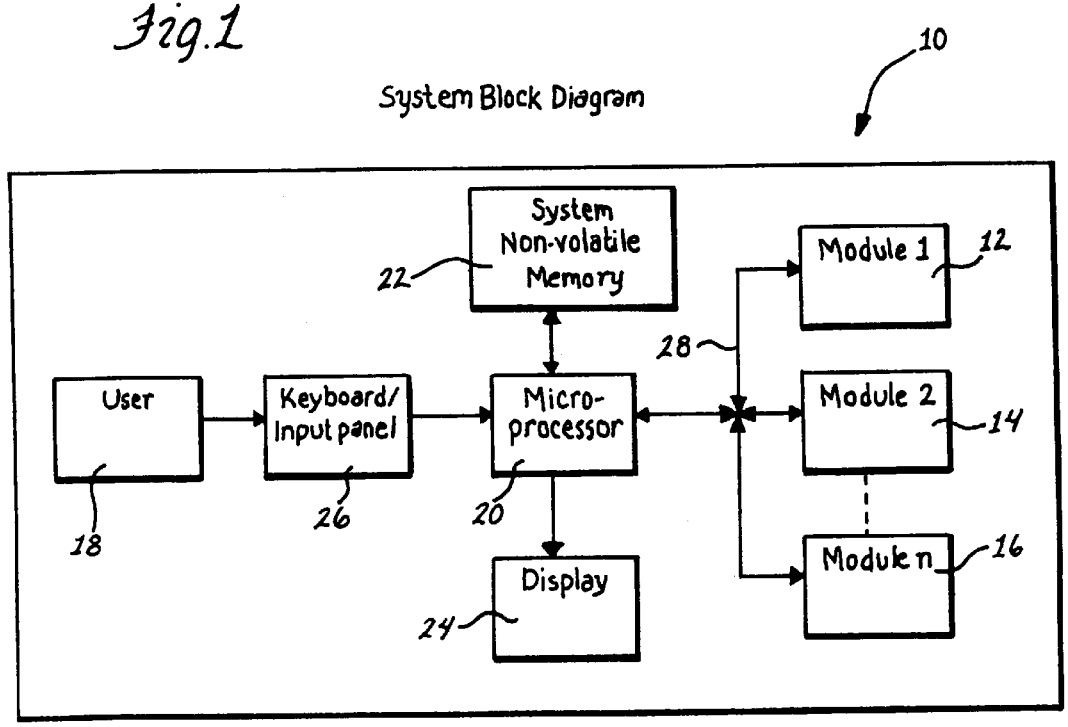
FIG. 1 is a system block diagram of a medical treatment device according to principles of the present invention.
Figure 2:
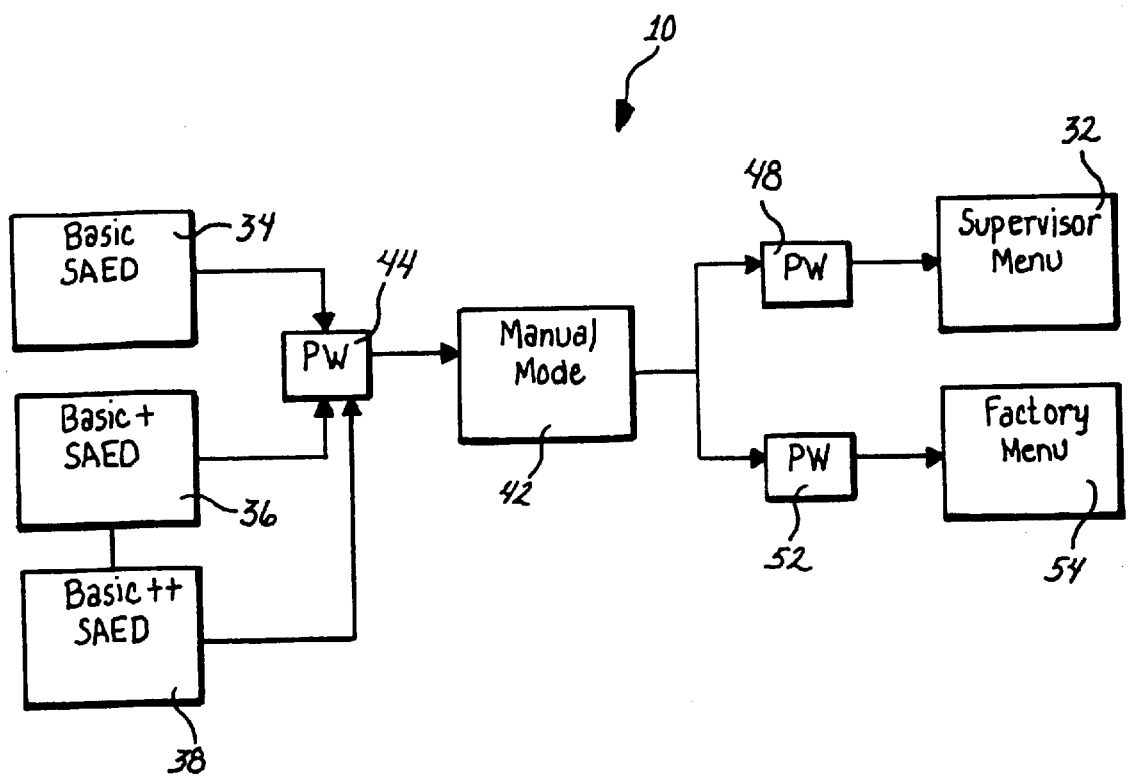
FIG. 2 is a schematic diagram of the operation thereof.

Referring now to FIGS. 1 and 2, a first embodiment of a medical treatment device is shown. As used herein, the term "medical treatment" refers not only to invasive and non-invasive intervention procedures, but also to patient monitoring procedures often, but not always, related to the intervention being contemplated. The medical treatment device 10 includes a plurality of medical treatment modules. Three such modules 12–16 are shown, although, as indicated by the dash line in FIG. 1, a greater number of modules is contemplated by the present invention.

Medical treatment device 10 provides a reduction in patient cost, particularly in those situations where members of a large population are to be protected against a variety of unforeseen medical emergencies. Although the medical treatment device 10 finds immediate practical application in the field of treating medical emergencies, the present invention also provides substantial benefits for routine patient treatment. In the most preferred embodiment, medical treatment module 12 is suitable for delivering cardiac defibrillation therapy on short notice. Most preferably, module 12 comprises only a cardiac defibrillator device, and controls for this are provided in microprocessor 20 or in other modules external to module 12. As will be seen herein, provision is made for multiple levels of operator control of the defibrillator operations that may be made available at any given time.

Figure 10:
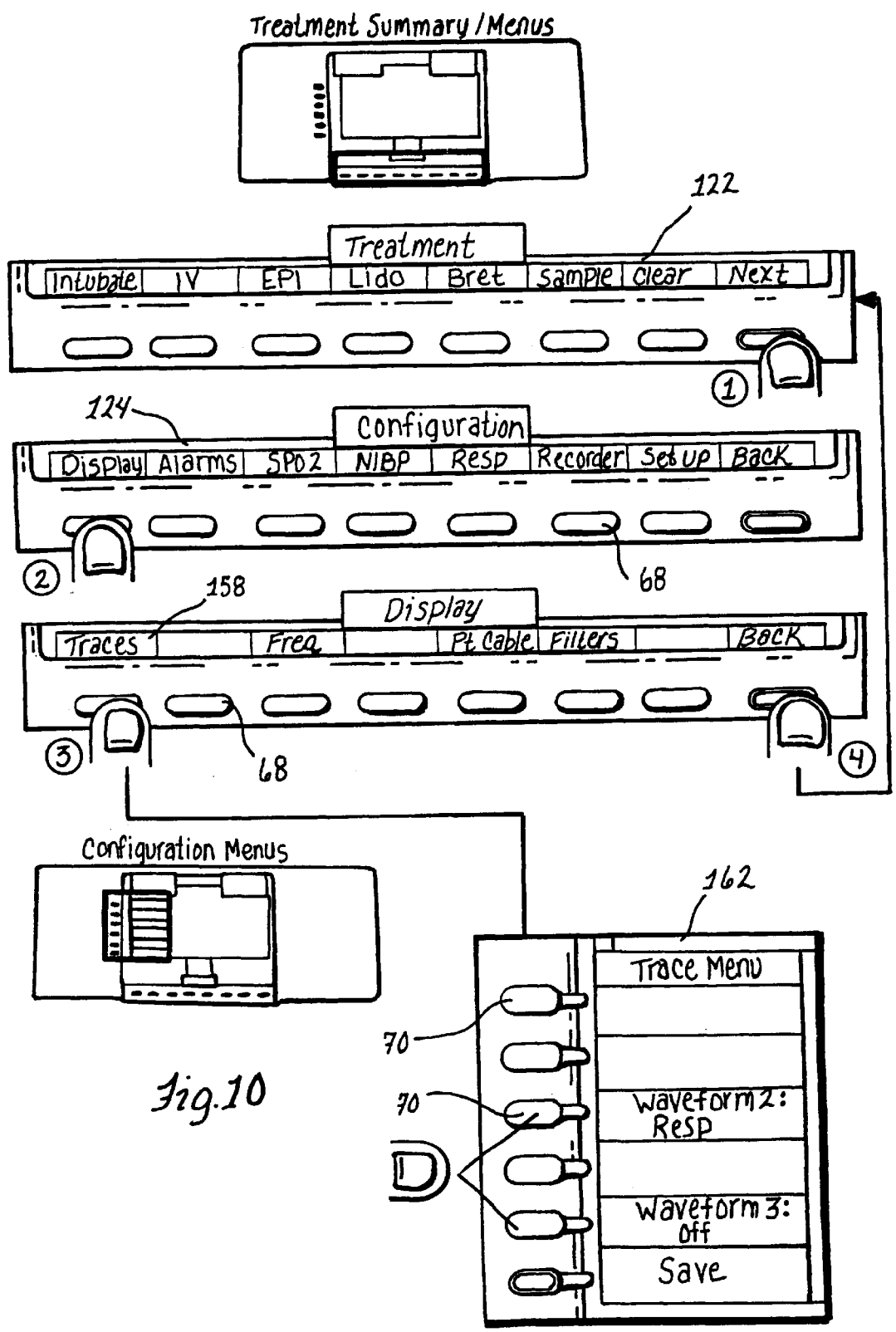
FIG. 10 is a schematic diagram showing a key press sequence for altering the device screen display.

In one aspect, the present invention is directed to medical treatment devices which may be operated by a number of different users 18 having, potentially, a wide range of medical training and including users having virtually no medical training at all. Accordingly, it is preferred that defibrillator module 12 has, with appropriate controls, defibrillation capability which is either fully automatic, semi-automatic, or manual. As indicated in FIG. 10, module 12 is coupled to a microprocessor 20 by a bus 28. Preferably, bus 28 has bi-directional capability such that one or more of the modules 12–16 can convey data to the microprocessor, as well as receiving operating instructions from the microprocessor, in either real time or previously installed automated program control.

Microprocessor 20 is of conventional construction and is supported by system non-volatile memory 22, a display 24 and input capability 26 preferably in the form of a keyboard or, alternatively, a touch screen, bio-metric reader (e.g., fingerprint, eye pattern) or other conventional input device. The input device could also comprise a radio, telephone, telefax or other receiver of electronic information from a remote device external to the medical treatment device. The input device 26 can have special purpose input options such as keys especially labeled for specific functions or, more preferably, input device 26 is of a general purpose, e.g., alphanumeric keyboard, with the keys being assigned functions which appear on display 24.

As mentioned, the present invention has found immediate acceptance for use with medical treatment devices having a plurality of different treatment modules. To supplement the defibrillator therapy of module 12, other modules could provide, for example, pacing therapy, as well as pulse oximeter data, blood pressure data, blood gas data and pulse data, for example. The remaining modules could also comprise, for example, a pre-amplifier associated with ECG functions, a printer for providing ECG traces or a log of medical treatment delivered during a medical treatment episode.

In its most preferred form, medical treatment device 10 can be readily employed by members of the general public as well as EMTs, nurses, physicians and other medical professionals having different levels of medical training. Accordingly, it is preferred that the medical device 10 be readily configurable, when required, so as to provide simple, uncomplicated medical treatment capability commensurate with safety and effective therapy concerns associated with members of the public at large. The advantages of automatic or semi-automatic external defibrillator therapy are being recognized by federal, state and local regulatory and governmental bodies. In light of an excellent safety record and high quality of beneficial medical treatment delivered, automatic and semi-automatic external defibrillators are considered safe for use by general members of the public. This represents a crucial advance in real-world practical medical treatment where medical intervention must take place within minutes if the patient's life is to be saved. Even in large cities having a large staff of trained and well equipped emergency personnel, several minutes may be lost before the personnel can reach the patient to deliver the proper life-saving therapy. Due to traffic delays and the length of travel time it required in the high rise elevators, emergency medical personnel may arrive too late to save a patient threatened by acute cardiac distress. Nationwide programs are now being proposed and implemented to make automatic and semi-automatic external defibrillators available on board an airplane, in office buildings, as well as in public and semi-public places.

In office settings, for example, co-workers can immediately deploy an automatic or semi-automatic external defibrillator if a fellow worker is suspected of experiencing acute cardiac distress. As is known, the external defibrillator device will automatically determine if cardiac shock therapy is appropriate, based upon patient data received by the defibrillator device. If the analytical functions of the defibrillator device determine that shock therapy is appropriate, the device will either deliver the therapeutic shock to the electrodes (automatic, AED mode), or will alert the user to depress a "fire" button (semi-automatic, SAED mode). If shock therapy is not recommended, the user will be so notified by the defibrillator device.

As mentioned, other treatment modules are included with the device, capable of delivering intrusive and non-intrusive therapies as well as patient monitoring. It may not be appropriate, for a variety of reasons, to allow an untrained user access to some of the medical treatment modules, or to retain functions contained in those modules. For example, it may not be appropriate to allow an untrained user to override an analytical capability of the external defibrillator, as this may unnecessarily expose the patient to a hazardous electrical shock condition. Further, it may not be appropriate to allow an untrained user to acquire various types of patient medical data as these data may be acquired under inappropriate conditions so as to be subject to substantial error.

Questions of patient confidentiality also arise. Print-outs of patient therapies administered and medical conditions observed may fall into the hands of non-medical personnel or others who are not responsible for preserving the patient's health. It may be desirable in such instances, to limit access to data output, and it may also be appropriate to limit data acquired from a patient, even though the data is stored within the medical treatment device and is not displayed or otherwise outputted at the scene of the emergency. Accordingly, as will be seen herein, steps are taken to restrict and at time positively preclude access to various features and capabilities of medical treatment device 10. In the preferred mode, access to higher level functions and capabilities is achieved by selective module enablement or module configuration triggered by a user's passcode, wherein module configuration alters the operation of a module, in accordance with the user's passcode.

Passcode operation of medical treatment device 10 is indicated with reference to the illustrated schematic diagram of FIG. 2. Operation of the device begins with boot-up of the operating system, when the medical treatment device is made operational by a user performing an initial cold boot operation, or a warm start or reboot operation. According to principles of the present invention, boot-up can be configured from the supervisor menu module 32 according to one of several options. In the first option, the system is booted with immediate entry into the basic SAED module 34. In this program module, only certain medical treatment modules of FIG. 1 are enabled. These modules include, for example, an ECG monitor module, an ECG analysis or expert module and an SAED defibrillator module. When the device is controlled by the "Basic" program or set-up control module 34, as will be seen herein, the other "Basic" modules 36, 38, and "Manual" defibrillator treatment modules are locked out, disabled or otherwise made unavailable to the operator, with access being gained only through proper multiple tier passcode procedure to be described herein. The SAED defibrillator medical treatment module in part, controls automatic charging of the defibrillator capacitors with the user being unable to attain direct access to capacitor charge operations. Further, the SAED defibrillator medical treatment module is enabled only by the on board analytical or ECG analysis module. For SAED operation, the ECG analysis medical treatment module sends a permissive signal to the SAED defibrillator medical treatment module, and the user is required to depress a "fire" button to discharge the defibrillator capacitors.

If a fully automatic external defibrillator operation is desired, then the SAED defibrillator medical treatment module is modified so as to automatically "fire" the defibrillator capacitors when receiving a permissive or enable signal from the expert ECG analysis medical treatment module. If desired, an intermediate warning can be given, alerting the user to avoid electrical contact with the patient receiving the defibrillator therapy. A timer/alarm module to be described herein may also be employed to automatically warn of an automatic discharge of the defibrillator capacitors.

As an option, the medical treatment device 10 can be booted under control of the set-up or control module 36, resulting in a "Basic+" SAED mode of operation. This mode of operation is similar to that of control module 34, indicated above, with the addition of certain features. Boot-up in control module 38 will result in "Basic++" SAED mode of operation adding further additional features. However, in all of the "Basic" control modules 34–38, defibrillation, with attendant capacitor charging and discharging, is performed under control of the expert ECG analysis patient treatment module, as described above. That is, the user is not granted access to the capacitor charge or energy selection functions.

Most preferably, the second level of operation implemented by control module 36 adds features of on board oximeter and blood pressure monitoring of the patient, in addition to the "Basic" SAED features implemented by control module 34. The third "Basic" mode of operation enabled by control module 38 adds further features such as the ability to manually de-energize the defibrillator capacitors. In the preferred embodiment, in either the Basic+ mode implemented by control module 36 or the Basic++ mode implemented by control module 38, additional functions made available include a limited treatment summary and limited log functions which record data are made available to the user. In some of the basic modes of operation under control of modules 34–38, data recording or log operations may be allowed. However, in the preferred embodiment, such recording operations are limited in scope, with features being withheld.

As mentioned, access to the supervisor menu in control module 32 allows the medical treatment device, including the recording and log features to be re-programmed so as to become available upon re-boot of the system. It is contemplated that the supervisor will be responsible for overseeing operations of different groups of service providers, with each group having its own configuration settings. These different settings have come to be called "shift" settings. Multiple control levels are implemented, with multiple tiers of shift settings implemented by the various control modules.

In a second tier or access level, a so-called "manual" mode is implemented by control module 42. Preferably, the control module 42 is provided with the capability of automatic operation settings, allowing the module to assume different "shift" modes. With increasing levels of skill and training, service providers are allowed to access a greater number of control features. In a preferred embodiment, access to control module 42 can be gained only by successful passage through passcode control module 44. As indicated in FIG. 10, initial start-up of the medical treatment device 10 initiates operation in one of three control modules 34–38 as determined by supervisor menu settings previously invoked in control module 32. In each of the three basic-level control modules a key press or other data entry operation is made possible to invoke the passcode control module 44.

Upon successful entry of an appropriate passcode, control is passed to manual mode control module 42. Passcode control can take several different forms. For example, in the simplest form, a passcode entry of any kind whatsoever can be allowed to permit entry into manual control module 42. As mentioned, one of the medical treatment modules in FIG. 1 could comprise data recording or logging devices, and accordingly the data entry under control of passcode module 44 can serve as a mere recording or logging of the user's input. If heightened security is desired, the format of the passcode entered could be checked. Further, a pre-assigned list of valid passcodes could be stored in system non-volatile memory block 22 shown in FIG. 1. After entry of the passcode, a comparison operation could be carried out by microprocessor module 20 to confirm the exact identity of one of the pre-authorized stored passcodes.

Once entry is gained to the manual control module 42, it is generally preferred that all of the medical treatment modules be enabled and/or configured to allow the user full functionality of the medical treatment device 10. It is generally preferred in such arrangements that the user be allowed full access to the defibrillation capability of the medical treatment device 10. This is typically implemented as so-called "manual" defibrillation control where the user is allowed to set the energy level, charge the defibrillation capacitors, configure the alarm limits and deliver the pulse at will under either automatic operation or operation where a firing button must be depressed.

In addition to manual defibrillation, one of the medical treatment modules energized preferably includes cardiac pacer capability, preferably of the external transcutaneous pacing type. Setting of the output current and the output delivery mode (either "demand" or "asynchronous") is made available to the user. Different ranges of settings may automatically be set by configuring the chosen modules to operate in a limited capacity, as correlated to a user's passcode authorization stored in memory. In addition, the user can be given the option to record a pace marker on display module 24.

For medical treatment modules including charting capability, the pace marker can be added to the output chart along with an indication of pacing parameters, defibrillation therapy and treatment summary which can be input by the user and automatically notated with an accurate time indication as well as patient parameter or system status. The user may enter, for example, certain key ACLS events, including IV, INTUBATION, EPI, LIDO, ATROP. In addition, the user can direct ECG markers to be recorded on the same chart.

In situations where medical treatment should not be given by service providers of lesser training, confusion is avoided by denying service providers of the basic entry levels 34–38 from inquiring into the possibility of recording, logging or charting key ACLS events which are inappropriate to the level of service being provided.

As indicated in FIG. 2, it is possible to enter two different control modules from the manual control module 42, upon entry of appropriate passcodes. From the manual control module 42 a supervisor can enter passcode control module 48, for example, by a key press (as indicated on display 24 by the manual control module 42). Upon appropriate resolution of the passcode entry in control module 48, control is passed to the supervisor control module 32 which, as indicated, puts a special screen on display module 24 shown in FIG. 1. While in the supervisor control module 32, a supervisor can reconfigure the medical treatment device, modifying the particular medical treatment modules and the electronically settable control functions available within those modules.

One important supervisory role, especially in larger service organizations, is to define the "personality" or "shift" settings of the various control modules. As mentioned, FIG. 2 depicts a three-tier arrangement in which the second tier (implemented by manual control module 42) is normally fully functional, making the complete set of medical treatment modules and functionality available to the user. It may, nonetheless, be desirable to limit certain inappropriate functions in the manual mode and, accordingly, a supervisor may wish to reconfigure features of the manual mode available to a user. For example, it may be desirable to set alarm limits, preselect possible custom drug annotations, or set the audio recording mode. Unused screens may be inhibited, particularly in situations where complex treatment scenarios are encountered, in order to avoid possible information overload.

It is generally preferred that, from the supervisor control module 32, the non-invasive blood pressure (NIBP) medical treatment module (see modules 12–16 of FIG. 1) be calibrated to withhold NIBP calibration from lower tier access levels. In the preferred embodiment, this feature is available only from the supervisor control module 32 which also allows the supervisor to set the temperature indications in either degrees C. or degrees F. format, as well as configuring the external pacer. If, for example, the pacer is made available to the higher basic levels (e.g., basic control module 38) the supervisor may limit the energy output of the pacer medical treatment module and can also set the default pacer mode of operation.

The supervisor can also set the energy output sequence or alternatively limit the maximum energy output of the automatic or semi-automatic external defibrillator medical treatment module made available in the basic control levels 34–38. As mentioned, it is generally preferred that the higher basic control levels allow access to a pulse oximeter medical treatment module. Preferably, this module is of a conventional type incorporating expert capability so as to identify pulse wave forms in the incoming data stream. Depending upon the organizational protocols, it may be desirable for the supervisor to "lock out" the pulse oximeter readings upon indication of a low perfusion condition, as the accuracy of the pulse oximeter readings may be compromised due to a weak pulse condition. As an intermediate control step, a supervisor may elect to send the operator a warning to remove any blood pressure cuff, tourniquet, or other flow restriction that may be present on the patient's arm where the pulse oximeter readings are taken, rather than to lock out operation of the pulse oximeter medical treatment module. As a further alternative, the supervisor may require a mandatory output indication that the pulse oximeter readings are suspect, and this may be of particular benefit where recording and logging capability are enabled for the particular "shift" setting.

Referring again to FIG. 2, a user in the manual mode (i.e., Manual control module 42) can enter a third tier control level by invoking passcode control module 52 in an effort to attain entry into the Factory control module 54. In the preferred embodiment, access to the Factory control module 54 is limited to the manufacturer of the medical treatment device or, on rare occasion, one of the manufacturer's field representatives. The factory control module 54 is preferably entirely unlimited, allowing access to every aspect of the medical treatment device 10. As mentioned above, it is generally preferred that the supervisor be allowed to configure most of the medical treatment device, although it is desirable to prevent even a supervisor from gaining entry to certain aspects of the device operation. For example, it is generally preferred that only the manufacturer be allowed to set the serial number of the particular medical treatment device, so as to enable compliance with federal, state and local governmental regulations. Other examples of settings usually made only by the manufacturer include reprogramming of the various control modules shown in FIG. 2, drivers and other software controls of the hardware modules indicated in FIG. 1 and running certain diagnostic routines to evaluate performance of the medical treatment device. As a further alternative, a manufacturer of the medical treatment device is usually asked to set the language selection of the various data screens appearing on display module 24 (see FIG. 1) at the time of manufacture. However, where medical service is provided near national or regional borders, it may be desirable to transfer control of language selection to lower service modules in the third tier (herein the supervisor control module 32) or to the lower tiers of device control (e.g., the second tier manual control module 42 or the first tier basic control modules 34–38).

The flexibility of operation afforded by the present invention provides a substantial cost benefit to the manufacturer in that the medical treatment device design, number of operational models and stocking of components is substantially reduced. Further, cost benefits are also made available to a user in that economically constructed medical treatment devices having robust capabilities can now be assigned to field personnel having varying levels of training and skills. Further benefits, both cost related and health related, are made possible by the present invention in that the medical treatment device, even if initially connected to the patient by a lower level service provider, can remain with the patient as patient care is transferred to a hospital and eventually to one or more attending physicians who can, with a simple procedure, acquire full control of the medical treatment modules and functionality offered by the medical treatment device. Thus, for example, the patient can be continuously monitored from the time of initial care and, if desired, the medical treatment device can remain connected to the patient, continuously, even during surgical procedures. Thus, a more flexible avenue of cooperation between field service providers and hospital staff can be enjoyed with medical treatment devices constructed according to principles of the present invention.

Figure 3:
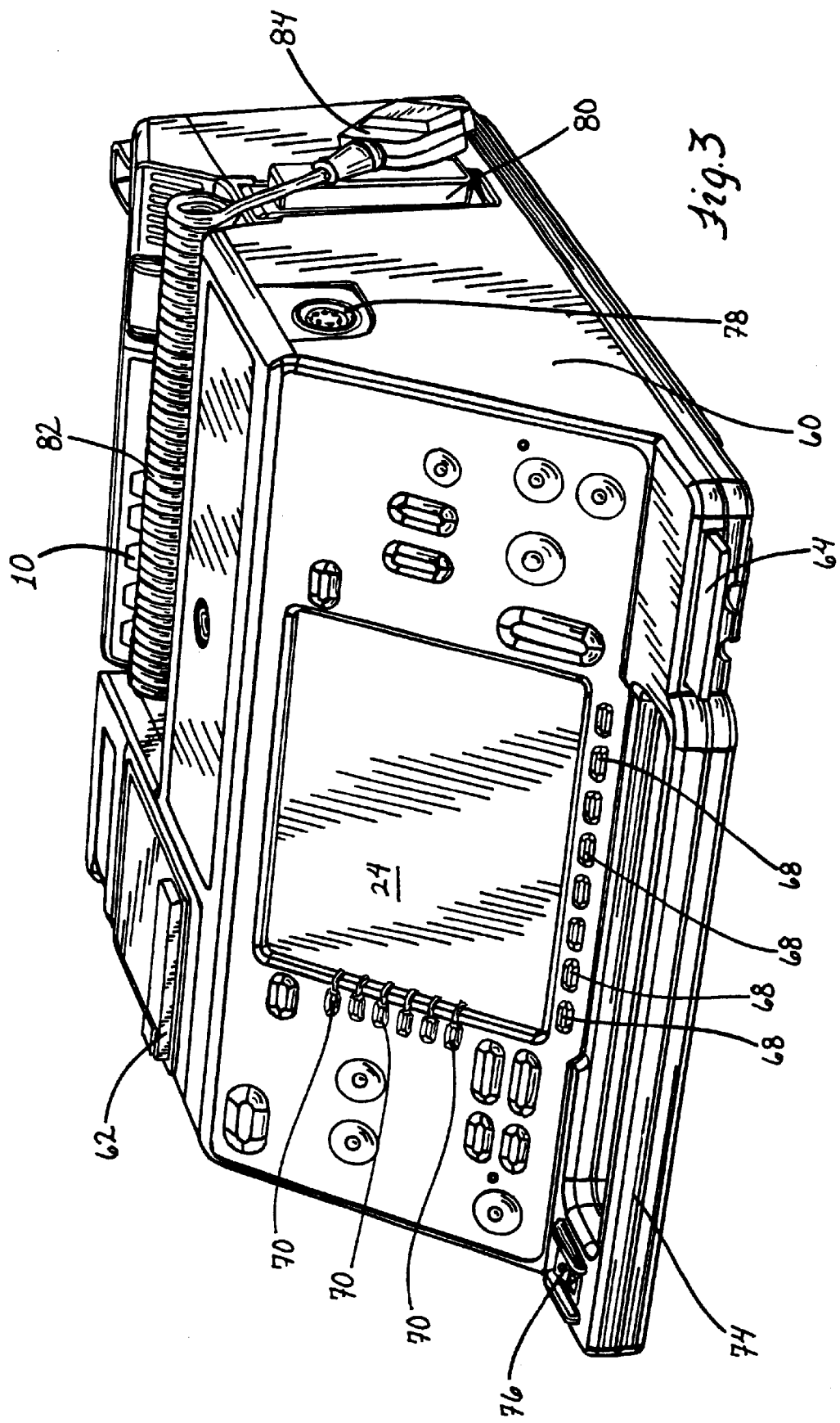
FIG. 3 is a perspective view of a medical treatment device according to principles of the present invention.

Referring now to FIG. 3, the medical treatment device 10 is shown incorporated in a housing 60 of plastic or other conventional material. One of the medical treatment modules includes a chart or strip printer 62. Another medical treatment device module illustrated is an input/output data device 64, preferably in the form of a PCMCIA interface. A row of eight key press buttons 68 are located at the bottom of display 24 and a row of six key press buttons 70 are located at the left-hand side of the screen display. As will be seen herein, the bottom row of keys 68 is used for menu selection while the side row of keys 70 is used for passcode entry and feature setting.

In the preferred embodiment, the medical treatment device 10 is fully self-contained and self-powered so as to be suitable for portable use. A carrying handle 74 is located to one side of input/output device module 64 and a unit "on/off" switch control 76 is incorporated in the handle. An ECG patient cable connector 78 is provided at the right-hand side of housing 60, adjacent a storage battery 80. A cable 82 is provided with a connector 84 for the connection of special purpose external defibrillator electrodes, non-invasive pacing pads or internal defibrillator paddle sets.

Figure 4:
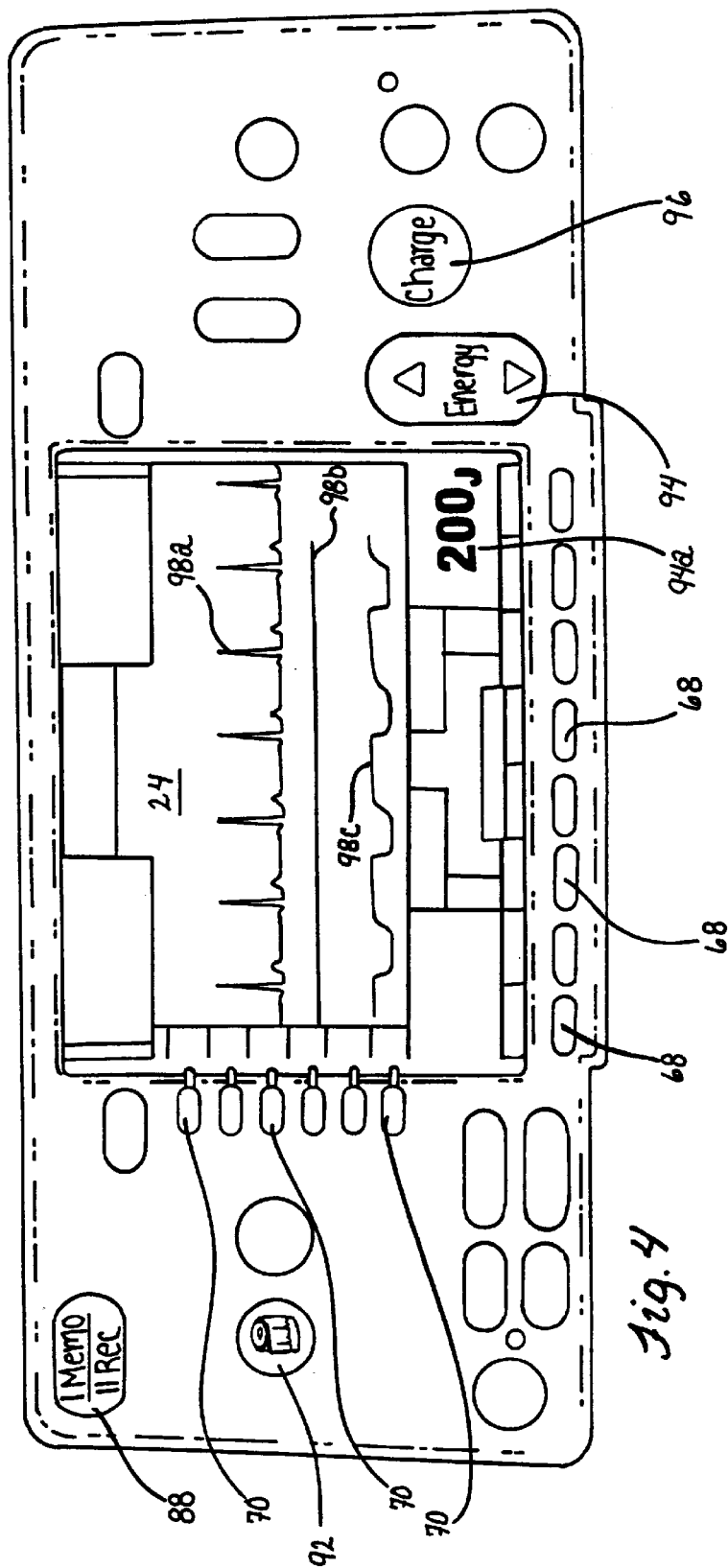
FIG. 4 shows the front panel thereof in greater detail.

In the preferred embodiment, one of the patient treatment modules includes a voice recorder and a push button 88 is provided to start and stop the voice recorder operation. A chart print button 92 controls operation of the chart recorder 62. Preferably, one of the medical treatment modules includes audible alerts corresponding to screen information output on display 24 and other voice prompts under control of the various control modules active at the time. An energy level setting button 94 and a defibrillator capacitor discharge button 96 are preferably made available to the user under operation of manual control module 42. The outputs of various medical treatment device modules is graphically displayed, as indicated by wave forms 98a–98c appearing on display 24. As can be seen from the brief description of the front panel shown in FIG. 4, passcode control according to principles of the present invention provides flexible operation allowing the "character" or "personality" of the medical treatment device to change considerably, depending upon the passcode employed and the automatic reconfiguration in response to the passcode entry.

Reference will now be made to FIGS. 5–10 which illustrate a number of key press sequences associated with passcode control according to principles of the present invention.

FIG. 5 shows a supervisor key press sequence, one example of a supervisor menu operation, under control of module 32 described above with reference to FIG. 2. As shown at the top of FIG. 5, the medical treatment device 10 is running under control of manual control module 42. The bottom of the front panel, including the row of buttons 68, has an initial appearance indicated by the reference numeral 102. The text indications appearing above the buttons 68 appear as part of the screen shown on display 24. The display portion indicated by reference numeral 102 pertains to various treatment procedures which can be entered in the patient's log or data recording modules (see reference numerals 12–16 in FIG. 1). As indicated, the last button 68 is pressed, causing the screen to change as indicated by reference numeral 104. As can be seen, a different range of functions is assigned to the buttons 68 and the display portion 104 is regarded as a "configuration menu". By pressing button 68 associated with the "Set-up" indication, a screen display is revised, showing the set-up menu indicated by reference numeral 106. One of the options displayed is to enter the supervisor control mode and with the appropriate key press indicated, an updated screen appears on display 24, adjacent the vertical array of buttons 70 as indicated by reference numeral 108. As can be seen in the display portion 108, passcode entry is requested under control of passcode control module 48 described above in FIG. 2. If the passcode is successfully entered and recognized by module 48, the screen on display 24 is updated as indicated by reference numeral 110. As indicated at 110, the supervisor has the ability to change defibrillator and pacer settings as well as changing the diagnostic (Diag) settings, and calibrating (Cal) various medical treatment modules. As indicated by the key press sequence, the supervisor "Set-Up" option is chosen, causing the screen on display 24 to change as indicated by reference numeral 112. In the particular example illustrated in FIG. 5, the supervisor selects the temperature format for configuration. In this particular example, only two choices are made available to the supervisor by the factory module 54 but more can be entered from Supervisor control module 32 if desired. Once the temperature settings are completed, the supervisor can "scroll" back to any of the preceding data screens.

Figure 6:
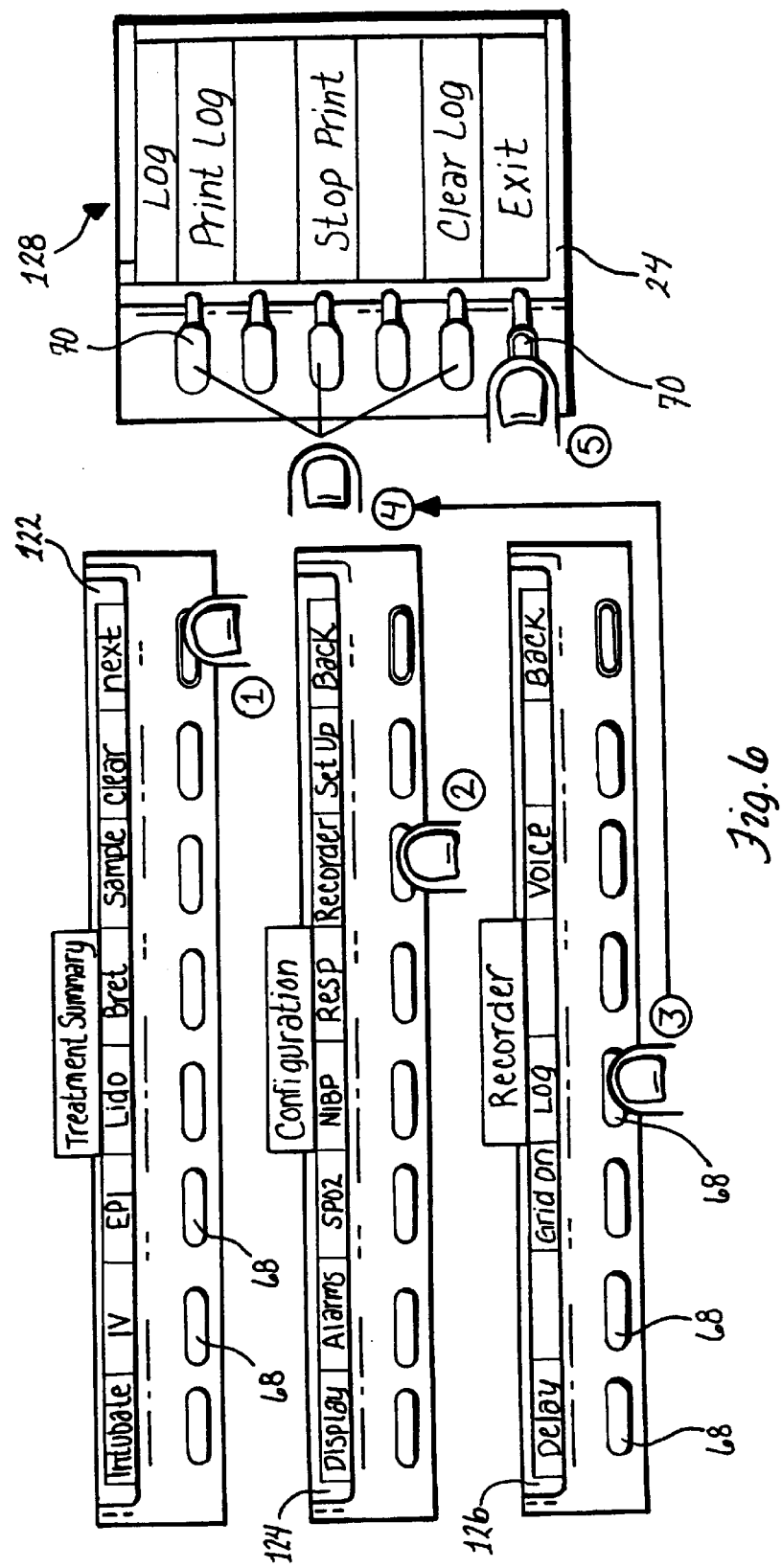
FIG. 6 is a schematic diagram indicating a key press procedure for controlling a chart and log patient treatment module.
Figure 7:
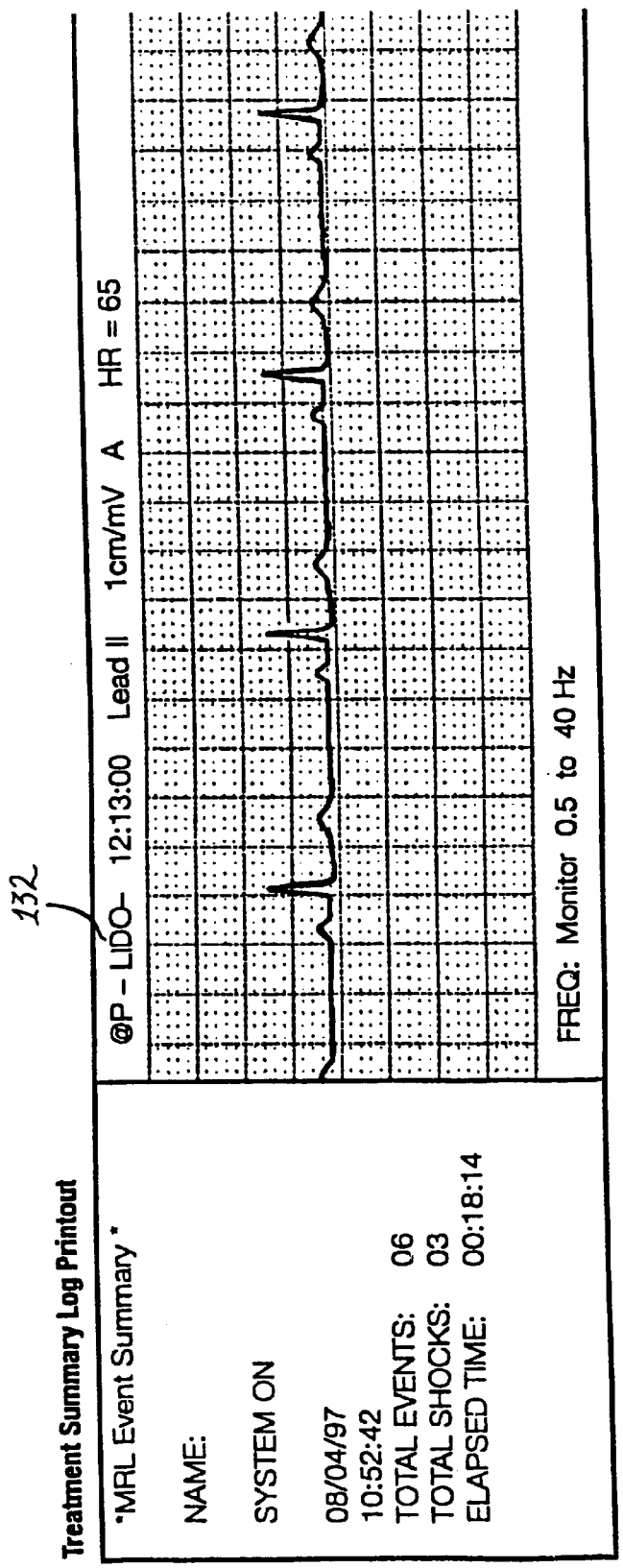
FIG. 7 shows a sample chart or log print-out.

FIG. 6 shows a recorder/log configuration operation. As indicated in "Fig. 6, a selection of the recorder "Log" operations is performed. Under operation of supervisor control module 32, the sequence indicated in FIG. 6 can be made available to any of the underlying tiers of control, but preferably is made available only in the higher basic levels (tier one) or the manual module 42 (tier two). Screens 122, 124, 126 are updated with the key press operation as indicated in FIG. 6. With the key press indicated with reference to screen portion 126, a control window 128 appears alongside the vertical array of buttons 70, at the left-hand side of display 24. As indicated in FIG. 6, two of the buttons 70 allow access to the strip printer module to initiate a print-out of stored "Log" data and to selectively stop the print-out. A third possibility is also presented to the user to clear the "Log", the usual reference to a "patient treatment summary." As a matter of procedure, the "Clear Log" function may be restricted to the higher tiers of control, preferably either the manual control module 42 in the second tier or the supervisor control module 32 in the third tier. FIG. 7 shows a sample print-out. A print-out of this type is usually associated with a patient "treatment summary". The print-out provides a hard copy recording of medical interventions and other actions taken by service personnel in the course of treating a patient. As indicated in screen portion 122 in FIG. 6, various medical intervention procedures are indicated, each with their associated data entry button 68. This allows a service provider to indicate what medical intervention was delivered, and by timing the data entry key pulse to the approximate time of the intervention procedure, a clock or time indication of the intervention procedure is also provided in the treatment summary log (see reference numeral 132 in FIG. 7). For a variety of reasons, it may be inappropriate or inadvisable to allow the user the opportunity to enter treatment intervention codes in the treatment summary log. As mentioned, the screen portion 122 indicating treatment summaries and other medical interventions is preferably made available only in the "manual" mode with the display 24 operating under control of manual control module 42. In lower, "tier one" shift settings, a screen portion 22 would not appear and the buttons 68 would not be configured to allow such entries in the treatment summary log.

Referring to FIG. 8, passcode control according to principles of the present invention can also be employed to alter the screens shown on display 24. It is assumed that operation is initiated in the manual mode of control, associated with control module 42. After passing through the screen portions 122, 124 entry is gained to a respiration monitor configuration indicated by reference numeral 136. As indicated at the bottom of FIG. 8, three different configuration menus 140, 142 and 144 are made to appear at that portion of the screen immediately adjacent the array of buttons 70. One or more buttons are enabled, corresponding to the screen indications illustrated. If desired, any of the configuration menus can be precluded from entry by a passcode control module, requiring a valid passcode entry before access is gained to the configuration menu in question.

Referring now to FIG. 9, a key press sequence is indicated to gain control via a recorder menu indicated by screen portion 148. A recorder menu indicated in the figure typically provides access to a variety of patient treatment devices (see reference numerals 12–16 in FIG. 1). Features of a voice recorder device module may be configured and recorded voice notations may be reviewed, according to the voice memo menu indicated by reference numeral 152 appearing to the right of buttons 70. The print log menu screen 128 discussed above with reference to FIG. 6 is accessible through the appropriate key press indicated in FIG. 9. A print grid menu screen 154 is also accessible to the user by pressing the button 68 adjacent the "Grid On" indication in screen portion 148. A print grid menu screen 154 is made to appear adjacent the buttons 70. It is desirable to limit access to at least some of the options illustrated in FIG. 9, which are made available to a user.

As has already been mentioned, it may be advisable in certain instances to preclude a user from clearing a stored log. In other instances, particularly the lower levels of "tier one" control modules, it may be desirable not to allow a user to print a treatment summary log. In the higher levels, it may be desirable to permit a user to print a simplified log showing certain notations only but excluding many of the data indications associated with treatments mode available to a user in the manual mode, under control of module 42. The passcode control features made available to a purchaser of the medical treatment device allows the ability for field personnel to quickly configure the device with a different "personality" via different "shift" settings set by a supervisor under control of module 32. While allowing the maximum appropriate flexibility to lower level users, a high level user (e.g., Supervisor) can, via the passcode entry system, impose restrictions on device functionality.

As mentioned above with reference to FIG. 8, configuration of the respiration screen and optionally associated data storage is made available to an appropriately authorized user. As indicated in FIG. 8, the graphical size, speed, and refresh rate can be set for the data trace of interest. With reference again to FIG. 4, three graphical traces may be generated from accumulated data and displayed to a user. In order to avoid information overload to a lower trained user for example, the display screen may be limited to one or two wave forms, in accordance with the key press sequence indicated in FIG. 10, and with appropriate key presses, the "display" menu on screen portion 158 is made available to the user. By depressing the button 68 adjacent the "Traces" portion of the screen, the "Trace Menu" window 162 appears adjacent buttons 70. In the particular embodiment illustrated, wave forms two and three can be toggled on and off by depressing the appropriate button 70. If desired, wave form one, the sole remaining wave form, can also be configured on or off in a similar manner.

Figure 11:
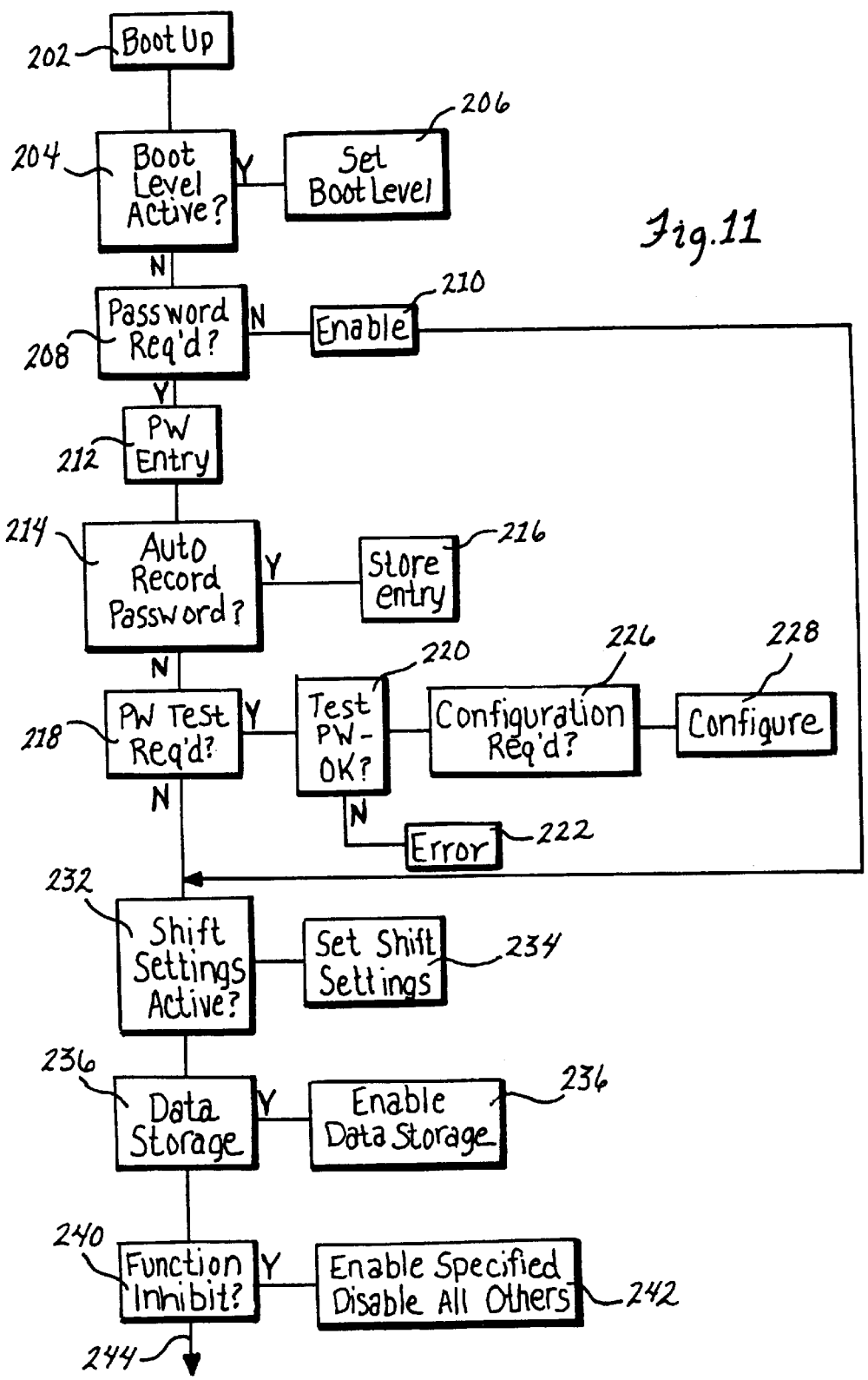
FIG. 11 is a schematic diagram indicating operation of the medical treatment device.

Referring now to FIG. 11, a sequence of operation of an alternative medical treatment device is shown. When the device is initially powered on, an automatic boot-up process is carried out by microprocessor 20, shown in FIG. 1. The boot-up process is indicated in FIG. 11 by reference numeral 202. A check is then made of certain registers in the system non-volatile memory module 22 to determine if the supervisor or factory has indicated that boot level control has been implemented and if so, the boot level is identified in module 204. If the boot level has been set, control is transferred to block 206 which enables the indicated boot control module (e.g., 34–38 in FIG. 2).

Program control is then passed to block 208 which determines from the system non-volatile memory module 22 whether a required passcode has been mandated, usually either by the supervisor or the factory. If a passcode is not required, control is transferred to the block 210 which enables the medical treatment device modules 12–16 (see FIG. 1).

Control is then passed to the shift settings block downstream of the passcode-related block. If a passcode is required, control is passed to the passcode entry block 212. Passcode entry is preferably carried out according to the key press sequence indicated at 108 in FIG. 5. However, other forms of passcode entry are also recognized by the present invention. These alternative forms of passcode entry include conventional data entry modes such as those using a touch screen, a finger print or other biometric scanner, tones or other coded information transmitted over a telephone, a facsimile connection, or a radio link to the microprocessor 20.

Data logging procedures are then initiated by passing control to block 214 which interrogates the system non-volatile memory 22 or other memory storage, to determine whether automatic recording of the passcode has been mandated. If so, control is passed to block 216 where the passcode entry and storage is performed. The storage of passcode entry information may, for example, be carried out in system non-volatile memory 22 or in a removable storage media 64 discussed above with reference to FIG. 3.

Control is then passed to block 218 to determine whether a testing of the passcode is required. If so, the passcode is tested in block 220 and if faulty, an error condition is given in block 222. Thereafter, further access to the medical treatment device may be precluded with further boot-up of the device being blocked until reset with an appropriate passcode entry or other security procedure which permits boot-up at least to the extent of accepting a passcode entry and testing the passcode entry for prior authorization.

The passcode test performed in block 220 can take a variety of forms, as discussed. The passcode test can range from entry of any type and of any length, to a match of at least the formatting of the passcode entry, to a required identify check to determine that the identical passcode has been previously authorized. Control is then transferred to block 226 which determines whether configuration of the medical treatment device modules or the functionality of those modules must be reconfigured from the condition at boot-up. The need for configuration is determined by block 226 and the control is passed to block 228 which sends the appropriate digital or other control signals to the various medical treatment modules or other equipment associated with medical treatment device 10. As will be seen shortly, control is passed to a shift settings module to set the "personality" of the medical treatment device. There is, accordingly, some overlap between the configuration carried out in block 228 and that subsequently carried out in the shift settings module. It is preferred that control block 228 be reserved for operation at the treatment module level, and that the shift settings be reserved for control of functionality within the treatment modules. It may be convenient from time to time, however, to control enablement of an entire treatment module from the shift settings control block.

As mentioned, control is then passed to the shift settings control block indicated by reference numeral 232. If the need to carry out shift settings is indicated, control is transferred to block 234 which carries out the required settings, usually settings within an enabled medical treatment module (e.g., modules 12–16 of FIG. 1). One example of a shift settings operation carried out under control of block 234 can be seen with reference to FIG. 8, discussed above. Assuming that the medical treatment display module and ECG patient treatment module have been enabled, the "personality" of the ECG trace can be automatically set by block 234 to accomplish the end result achieved by the key press sequence indicated in FIG. 8. In one aspect, the shift settings can be seen to operate in a manner similar to keyboard and macro operations associated with programmable digital computers.

The operational routine illustrated in FIG. 11 can provide for specific patient treatment modules to override or otherwise avoid the effects of configuration of control block 228 or shift setting control block 234. One example is given in control block 236 which determines whether accumulated data is to be stored, independent of a user's preference. For example, certain supervisors can be allowed to configure the patient treatment log, to determine whether data inputs are shown on display 24 as well as determining the nature and character of the data involved. It may be desirable in certain instances to store all data accumulated by a medical treatment device in an unformatted or minimally formatted state. If this functionality is desired, control is transferred to control block 238 which routes all accumulated data signals to a designated storage device, which presumably is made available to a user only upon a higher level passcode entry.

Finally, FIG. 11 illustrates the possibility of going beyond previous passcode-controlled settings to positively inhibit certain designated treatment modules or functions within those modules. Control is transferred to block 242 which can operate in a number of different ways. For example, as indicated in FIG. 11, two groups of functions can be identified, one to be enabled and the others to be positively disabled, so as to guarantee that their functionality will not be available. Alternatively, control block 242 can be set up to merely positively disable those selected functions and/or medical treatment modules. In the preferred embodiment, control then continues as indicated by 244, to the boot control module indicated by control block 206.

Figure 12A:
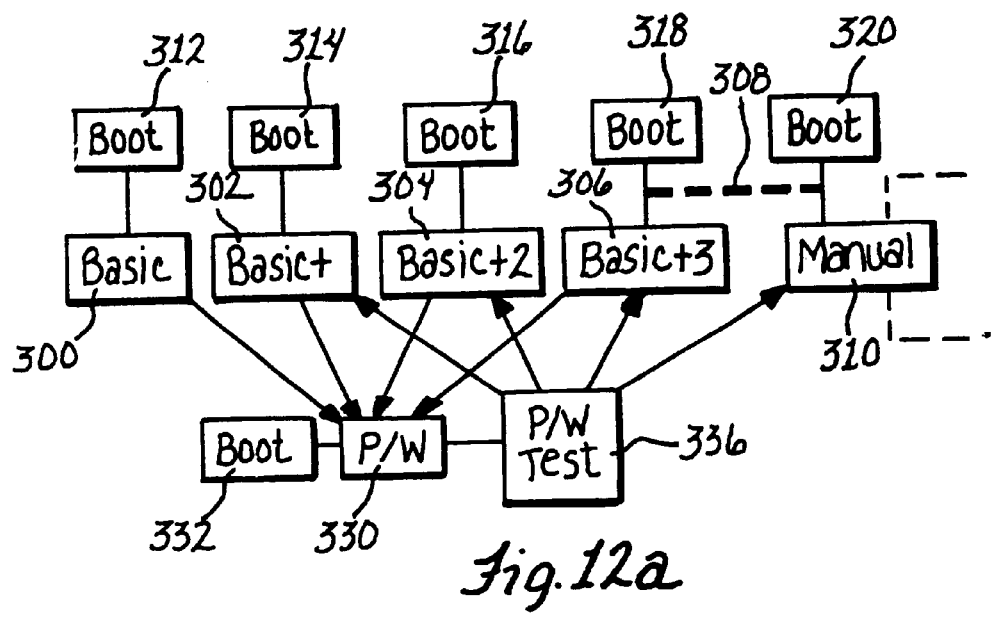
FIGS. 12a and 12b together comprise a schematic diagram of the medical treatment device operation.
Figure 12B:
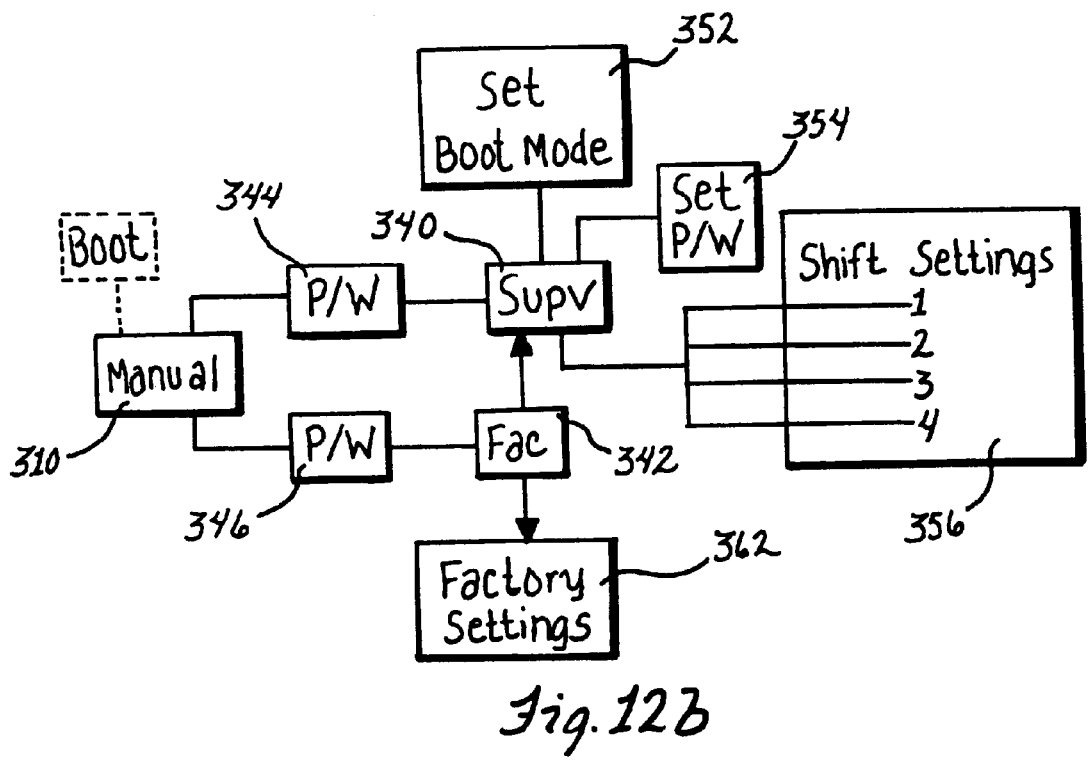

It is also possible to employ passcode control to permit passage between various control modules, without requiring an intervening re-boot of the medical treatment device. Referring to FIGS. 12a and 12b, a schematic diagram is shown indicating flexibility of passcode systems according to the principles of the present invention. As shown in FIG. 12a, a number of different entry points into the medical treatment device are made possible on boot-up. Four different basic modes of operation are indicated at 300–306. The dash line indicates that other intervening tiers or individual control elements are possible, but not shown. In control module 310, a higher level of control, preferably one similar to the manual control module 42, is made available in a number of different ways. For example, as can be seen in FIG. 12a, each of the control modules 300–310 can be accessed directly upon boot-up, as indicated by blocks 312–320.

As indicated by schematic lines, entry may be gained from any of the basic level control blocks 300–306 to passcode control block 330. Under control of block 330, passcode entry is enabled and acquired, for example, in a manner similar to that indicated by reference numeral 108 in FIG. 5. Alternatively, it is possible to enter passcode control block 330 directly upon boot-up, as indicated by control block 332. The option to enable or disable control block 332 may be set by a supervisor as in supervisor control block 32 of FIG. 2 or by lower control level as may be permitted by the supervisor. Once the passcode has been acquired, control is transferred to block 336 which tests the passcode according to routines prescribed either by the supervisor or the factory. If the passcode is deemed acceptable, control is then transferred to higher level control blocks, including the manual control block 310. If desired, control block 336 can transfer control to a lower level, but this is rarely done and provision of this type is normally not required. Referring to FIG. 12b, once control is passed to block 310, a supervisor or authorized factory representative can gain entry to the higher control levels indicated by control 340, 342. The intervening passcode control blocks 344, 346 could effectively be eliminated, if desired, by overriding the need to acquire a valid passcode.

Once control is gained in module 340, a supervisor can, as mentioned, set the treatment device boot mode as indicated by control block 352, set any of the passcodes mentioned herein, as indicated by control block 354 or can set any of the shift settings, herein designated as shift settings 1–4, as indicated in control block 356. In the factory control module 342, the factory settings may be made as indicated by control module 362 or, alternatively, entry can be made to the supervisory control module 340. Certain unusual unforeseen operating conditions can be easily accommodated by controlling treatment devices according to the present invention. For example, as has been pointed out above, the preferred medical treatment device includes most, if not all, of the capabilities required in intensive care situations.

Because the capabilities are embodied in a portable unit, roughly the size of a small suitcase, it is possible to encounter difficulties not present in traditional intensive care settings. For example, emergency medical care givers can operate along political or other boundaries having different medical protocols. The medical care givers could be required to conform to the medical protocols of any of the given authorities, at any given time. With the flexibility of operation provided, medical treatment devices can now be readily re-configured so as to conform to any local medical protocols that may be required, with the assurance to the responsible authorities that other inconsistent protocols are positively disabled.

In one possible scenario, an airline passenger may suddenly exhibit acute cardiac distress requiring immediate defibrillator, pacer or other medical treatment. Medical treatment devices carried on board the airliner can be rapidly employed by members of the general public, i.e., other airline passengers, airline personnel having a low level of intensive care training, or possibly a medical professional such as a trained EMT or physician. The same medical treatment device can be employed by all of the potential care givers, each care giver being allowed to operate only within a realm appropriate to their training and skill. In a manner similar to that indicated above, upon arrival at a destination, the patient can be carried off of the airliner with the medical treatment device remaining connected so as to provide constant care. The patient could, for example, be transferred to an ambulance having EMT trained personnel or paramedics and the same medical treatment device can be readily re-configured to accommodate their level of skill. Again, at arrival at the hospital, the medical treatment device can remain with the patient accompanying the patient into an emergency room or even an operating room, if required.

Each of the different treatment locations could conceivably fall under the responsibility of different medical professionals, each of which could, now or at some time in the future, conceivably have differing treatment protocols. It is now possible to readily implement the different medical treatment protocols simply and easily with medical treatment devices according to the present invention, and the passcode control systems can be employed to guarantee that inappropriate or undesirable medical treatments are positively prohibited. Such capabilities can be of considerable importance during times of national and international tragedies where medical care givers from other states or countries could be called in to help on an emergency basis, and given flexible medical treatment devices according to the principles of the present invention. It may not be possible to provide the visiting care givers with the required passcode or a trained care giver may find themselves at a disaster scene without planning to do so. With simple telephone and radio procedures, for example, it may now be possible to verify the proficiency and certification of the care giver and the appropriate passcode could be given on an immediate basis to allow virtually unpostponed emergency medical treatment, while ensuring that inappropriate and undesired medical protocols are not permitted by the medical treatment device. A passcode control module could be set up to allow a user access to the medical treatment device until the system is shut down. Alternatively, the passcode could have a limited duration set either by time, or by treatment given. For example, a passcode could allow a user to deliver a set number of therapeutic shocks, after which the user would have to contact the appropriate authorities for a new passcode.

Figure 13:
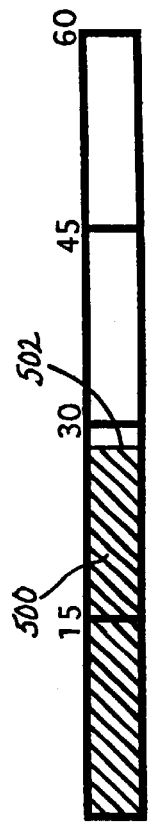
FIG. 13 shows a separation of a timer module.

As mentioned, alarm and timer functions can be integrated with passcode protection procedures to obtain increased performance. One example of a pop-up timer/alarm feature is shown in FIG. 13. A "thermometer" type of display travels through four marked zones, as illustrated. For example, in certain situations, a single defibrillation treatment may not result in the desired intervention. In the semi-automatic mode, a pre-determined sequence of treatments is invoked under program module control. In these sequences, a number of defibrillation events are defined, with time intervals between the defibrillator therapies, and with CPR intervention worked into the sequence. During CPR therapy, for example, the analysis module(s) of the medical treatment device will detect patient conditions which are unexpected. In order to prevent erroneous analysis, input to the analysis module(s) are preferably inhibited while CPR therapy is being administered. Because of the close timing involved in the sequence procedure, it may be helpful to inform a user of a time period during which analysis inputs are inhibited. A pop-up timer can be employed to provide visual and audible indication to the user of the progress of the pre-defined treatment sequence.

By way of a further example, the alarm/timer function can be implemented in a passcode control situation where a limited duration passcode mode has been mandated. A warning similar to that shown in FIG. 13 can be given to the user that the temporary passcode is about to expire, either with or without remedial action being made available. The alarm/timer function is also useful in other types of passcode or treatment events, as when a passcode-protected automatic blood pressure cycle is being performed. The timer/alarm function can also be used d ring a passcode protected calibration procedure when pulse-detecting modules are being evaluated.

As indicated in FIG. 2, six control modules are provided. According to principles of the present invention, the control modules are arranged in a plurality of tiers, some of which have multiple control modules and one of which has a single control module. Generally speaking, the tiers are arranged in quantum increases of functionality available to a user, while control levels within a given tier are associated with smaller, less significant increases of functionality. Referring to FIG. 2, a first tier includes control modules 34–38. The passcode module 44 separates the first tier from a second tier which includes the manual mode control module 42. As will be seen herein, it is generally preferred that in the manual mode, all of the medical treatment device functionality is made available to a user. A third tier includes control modules 32 and 54 and may be separated from the second tier by a single passcode control module although it is generally preferred that a passcode control module be provided for each control module of the third tier. Passcode protection is inherent in the first tier, although passcode control modules are not shown within the tier. Passcode control is implemented by determining beforehand which control module within the first tier is to become active upon boot-up of the medical treatment device. If desired, passcode control modules could be provided between the control modules of the first tier (see FIG. 12a), although this has not been found to be necessary. Rather, it has been found more practical to allow a user booting up in the first tier to gain access to the supervisor control module 32 in the third tier by entering appropriate passcodes in passcode control modules 44 and 48. While in the supervisor control module 32, the default control module 34–38 invoked on boot-up is set by storing appropriate command information in system nonvolatile memory 22 (see FIG. 1). Thus, it can be seen that the passcode control illustrated in FIG. 2 provides a two-dimensional array of control modules.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being deli for storing passcode data, delineated by the following claims.

What is claimed is:

1. A medical treatment device, comprising:
   a plurality of digitally controlled medical treatment modules arranged in multiple tiers, with at least one medical treatment module in each tier;
   a digital controller for controlling said plurality of medical treatment modules;
   memory storage means associated with said digital controller for storing passcode data;
   data entry means for entering user passcode data;
   comparator means for comparing the passcode data entered to the passcode data stored in said memory storage means, said comparator means determines authorized medical treatment modules authorized for the user and for delivering instructions to said digital controller to enable said authorized medical treatment modules;
   at least one of said tiers of said medical treatment modules including entry means permitting entry from another tier only upon user entry of a required passcode; and
   said data entry means comprises means for entering textual or biometric data.

2. The medical treatment device of claim 1 wherein said passcode data includes boot-up system boot-up passcode data, one of said multiple tiers comprises a supervisor tier for setting or altering said system boot-up passcode data in said memory storage means.

3. The medical treatment device of claim 1 wherein one of said multiple tiers comprises a supervisor tier for setting authorized passcode data for users of said medical treatment device.

4. The medical treatment device of claim 1 wherein one of said multiple tiers comprises a supervisor tier for setting or altering the medical treatment modules authorized for users of said medical treatment device.

5. The medical treatment device of claim 1 wherein one of said medical treatment modules comprises defibrillator means for delivering cardiac defibrillator treatment to a patient.

6. The medical treatment device of claim 1 wherein another of said medical treatment modules comprises defibrillator control means for controlling operation of said defibrillator means.

7. The medical treatment device of claim 1 wherein one of said medical treatment modules comprises pacing means for delivering cardiac pacing treatment to a patient.

8. The medical treatment device of claim 7 wherein another of said medical treatment modules comprises pacing control means for controlling operation of said pacing means.

9. The medical treatment device of claim 1 wherein one of said medical treatment modules comprises visual display means for presenting instructions that the user is allowed to enter so as to control other medical treatment modules which are authorized for the user.

10. The medical treatment device of claim 1 wherein said data entry means comprises means for entering user identification data.

11. The medical treatment device of claim 1 wherein said set-up means also configures at least one of said authorized medical treatment modules so as to specify the operation thereof.

12. A medical treatment device, comprising:
    a plurality of digitally controlled medical treatment modules arranged in multiple tiers, with at least one medical treatment module in each tier;
    a digital controller for controlling said plurality of medical treatment modules;
    memory storage means associated with said digital controller for storing passcode data;
    data entry means for entering user passcode data;
    comparator means for comparing the passcode data entered to the passcode data stored in said memory storage means, said comparator means determining authorized medical treatment modules authorized for the user and for delivering instructions to said digital controller to enable said authorized medical treatment modules;
    at least one of said tiers of said medical treatment modules including entry means permitting entry from another tier only upon user entry of a required passcode; and
    said data entry means comprises means for receiving electronic information from a remote device external to said medical treatment device.

13. The medical treatment device of claim 12 wherein said passcode data includes boot-up systems boot-up passcode data, one of said multiple tiers comprises a supervisor tier for setting or altering said system boot-up passcode data in said memory storage means.

14. The medical treatment device of claim 12 wherein one of said multiple tiers comprises a supervisor tier for setting authorized passcode data for users of said medical treatment device.

15. The medical treatment device of claim 12 wherein one of said multiple tiers comprises a supervisor tier for setting or altering the medical treatment modules authorized for users of said medical treatment device.

16. The medical treatment device of claim 12 wherein:
    one of said medical treatment modules comprises defibrillator means for delivering cardiac defibrillator treatment to a patient; and
    another of said medical treatment modules comprises defibrillator control means for controlling operation of said defibrillator means.

17. The medical treatment device of claim 12 wherein:
    one of said medical treatment modules comprises pacing means for delivering cardiac pacing treatment to a patient; and
    another of said medical treatment modules comprises pacing control means for controlling operation of said pacing means.

18. The medical treatment device of claim 12 wherein one of said medical treatment modules comprises visual display means for presenting instructions that the user is allowed to enter so as to control other medical treatment modules which are authorized for the user.

19. The medical treatment device of claim 12 wherein said data entry means comprises means for entering user identification data.

20. The medical treatment device of claim 12 wherein said set-up means also configures at least one of said authorized medical treatment modules so as to specify the operation thereof.

* * * * *